(12) United States Patent
Heiskanen

(10) Patent No.: US 10,729,931 B2
(45) Date of Patent: Aug. 4, 2020

(54) GARMENT

(71) Applicant: Vaskia Oy, Oulu (FI)

(72) Inventor: Marika Heiskanen, Oulu (FI)

(73) Assignee: VASKIA OY, Oulu (FI)

( * ) Notice: Subject to any disclaimer, the term of this patent is extended or adjusted under 35 U.S.C. 154(b) by 446 days.

(21) Appl. No.: 15/309,200

(22) PCT Filed: May 7, 2015

(86) PCT No.: PCT/FI2015/050311
§ 371 (c)(1),
(2) Date: Nov. 6, 2016

(87) PCT Pub. No.: WO2015/170011
PCT Pub. Date: Nov. 12, 2015

(65) Prior Publication Data
US 2017/0072250 A1  Mar. 16, 2017

(30) Foreign Application Priority Data

May 8, 2014  (FI) .................................... 20145422

(51) Int. Cl.
*A63B 21/00* (2006.01)
*A63B 21/055* (2006.01)
(Continued)

(52) U.S. Cl.
CPC .......... *A63B 21/4025* (2015.10); *A41D 1/002* (2013.01); *A41D 13/0015* (2013.01);
(Continued)

(58) Field of Classification Search
CPC ........ A63B 21/00061; A63B 21/00278; A63B 21/00185; A63B 21/002; A63B 21/0407;
(Continued)

(56) References Cited

U.S. PATENT DOCUMENTS 4,089,064 A * 5/1978 Chandler, Jr. ....... A41B 11/003
2/404
4,216,547 A * 8/1980 Picchione .......... A41D 13/0015
2/22
(Continued)

FOREIGN PATENT DOCUMENTS

CA        2756969 A1    5/2013
DE    102007051423 A1    4/2009
(Continued)

OTHER PUBLICATIONS

Authorized Officer Sara Teissier, EPO, Supplementary European Search Report, Application EP 15 78 8949, dated Dec. 11, 2017, pp. 1-2.

(Continued)

*Primary Examiner* — Anne M Kozak
(74) *Attorney, Agent, or Firm* — Otterstedt, Wallace & Kammer, LLP

(57) ABSTRACT

The invention relates to a garment for sports, health exercise, physiotherapy or another performance, the garment comprising a body part (BP) of the garment and one or more limb parts (L1, L2, H1, H2) of the garment which extend from the body part of the garment. The garment comprises one or more elastic reinforcements (B1, B2, B3) routed in the garment in accordance with one or more fascial lines (FL1, FL2, FL3) of a human body. The elastic reinforcements form a network, being provided both on a front side of the garment and a rear side of the garment.

1 Claim, 4 Drawing Sheets

(51) Int. Cl.

| | |
|---|---|
| *A61H 39/04* | (2006.01) |
| *A41D 13/00* | (2006.01) |
| *A41D 1/00* | (2018.01) |
| *A61N 2/06* | (2006.01) |
| *A61N 1/04* | (2006.01) |
| *A63B 21/002* | (2006.01) |
| *A63B 21/04* | (2006.01) |

(52) U.S. Cl.
CPC ........... *A61H 39/04* (2013.01); *A61N 1/0484* (2013.01); *A61N 2/06* (2013.01); *A63B 21/002* (2013.01); *A63B 21/00061* (2013.01); *A63B 21/00178* (2013.01); *A63B 21/00185* (2013.01); *A63B 21/0407* (2013.01); *A63B 21/0555* (2013.01); *A63B 21/0557* (2013.01); *A63B 21/4005* (2015.10); *A63B 21/4007* (2015.10); *A63B 21/4009* (2015.10); *A63B 21/4011* (2015.10); *A63B 21/4013* (2015.10); *A63B 21/4015* (2015.10); *A63B 21/4017* (2015.10); *A63B 21/4019* (2015.10); *A63B 21/4021* (2015.10); *A63B 21/4043* (2015.10); *A61H 2201/0107* (2013.01); *A61H 2201/165* (2013.01); *A61H 2201/1614* (2013.01); *A61H 2201/1619* (2013.01); *A61H 2201/1628* (2013.01); *A61H 2201/1635* (2013.01); *A61H 2201/1642* (2013.01); *A61H 2201/1685* (2013.01); *A61H 2201/1695* (2013.01); *A61H 2201/5092* (2013.01); *A61H 2230/60* (2013.01)

(58) Field of Classification Search
CPC ............ A63B 21/0555; A63B 21/0557; A63B 21/4005; A63B 21/007; A63B 21/4009; A63B 21/2011; A63B 21/2013; A63B 21/1015; A63B 21/4017; A63B 21/4019; A63B 21/4021; A63B 21/4043; A41D 1/002; A41D 13/0015; A61H 39/04; A61N 1/0484; A61N 2/06
USPC .......................................................... 2/311
See application file for complete search history.

(56) References Cited

U.S. PATENT DOCUMENTS

| | | | | |
|---|---|---|---|---|
| 4,862,523 A * | 9/1989 | Lipov | .................... | A41B 11/14 2/409 |
| 5,109,546 A * | 5/1992 | Dicker | ............... | A41D 13/0015 2/227 |
| 5,201,074 A * | 4/1993 | Dicker | ............... | A41D 13/0015 2/227 |
| 5,263,923 A * | 11/1993 | Fujimoto | ........... | A41D 13/0015 602/62 |
| 5,857,947 A | 1/1999 | Dicker et al. | | |
| 6,047,406 A * | 4/2000 | Dicker | ............... | A41D 13/0015 2/115 |
| 6,430,752 B1 * | 8/2002 | Bay | ........................ | A41C 1/003 2/228 |
| 7,945,970 B2 * | 5/2011 | Belluye | .............. | A41D 13/0015 2/227 |
| 8,296,864 B2 * | 10/2012 | Torry | ...................... | A41D 1/08 2/69 |
| 8,533,864 B1 * | 9/2013 | Kostrzewski | ...... | A41D 13/0015 2/69 |
| 8,707,463 B2 * | 4/2014 | Orloff | ................ | A41D 13/0015 2/22 |
| 8,887,315 B2 * | 11/2014 | Boynton | ................. | A61F 5/026 2/24 |
| 9,009,863 B2 * | 4/2015 | Decker | .................... | A41B 1/08 2/44 |
| 9,144,252 B1 * | 9/2015 | Kostrzewski | ...... | A41D 13/0015 |
| 9,226,534 B2 * | 1/2016 | Puni | .................. | A41D 13/0512 |
| 9,498,665 B2 * | 11/2016 | Warren | .............. | A41D 13/0015 |
| 9,622,518 B2 * | 4/2017 | Wright | ............... | A41D 13/0015 |
| 9,636,261 B2 * | 5/2017 | Mitsuno | .................. | A61F 13/08 |
| 9,895,569 B2 * | 2/2018 | Yao | .................... | A63B 69/0028 |
| 10,039,330 B2 * | 8/2018 | Tanaka | ..................... | A41D 1/08 |
| 2002/0143373 A1 * | 10/2002 | Courtnage | ............... | A61N 1/32 607/91 |
| 2004/0255358 A1 * | 12/2004 | Ota | ..................... | A41D 13/0015 2/69 |
| 2005/0187071 A1 * | 8/2005 | Yamashita | ......... | A41D 13/1236 482/1 |
| 2005/0193461 A1 * | 9/2005 | Caillibotte | ......... | A41D 13/0015 2/69 |
| 2005/0240134 A1 * | 10/2005 | Brown | .................. | A61F 5/0106 602/26 |
| 2007/0022510 A1 * | 2/2007 | Chapuis | ............. | A41D 13/0015 2/69 |
| 2007/0033696 A1 * | 2/2007 | Sellier | ................ | A41D 13/0017 2/69 |
| 2007/0111868 A1 * | 5/2007 | Fujii | .................. | A41D 13/0015 482/124 |
| 2010/0010568 A1 * | 1/2010 | Brown | .............. | A41D 13/0015 607/48 |
| 2010/0256717 A1 * | 10/2010 | Brown | .................... | A61F 5/026 607/115 |
| 2012/0238923 A1 | 9/2012 | Yamashita et al. | | |
| 2013/0012853 A1 | 1/2013 | Brown | | |
| 2013/0211302 A1 * | 8/2013 | Brown | .................... | A61F 5/026 602/19 |
| 2013/0326785 A1 * | 12/2013 | Cornacchiari | ........... | A41D 1/00 2/69 |
| 2014/0070957 A1 * | 3/2014 | Longinotti-Buitoni | ..................... | A61B 5/6804 340/870.01 |
| 2015/0366504 A1 * | 12/2015 | Connor | ................ | A61B 5/6804 600/301 |
| 2016/0008206 A1 * | 1/2016 | Devanaboyina | ....... | A47C 9/002 601/136 |
| 2016/0058657 A1 * | 3/2016 | Lal | ......................... | A61H 23/02 601/134 |

FOREIGN PATENT DOCUMENTS

| | | |
|---|---|---|
| FR | 2957809 A1 | 9/2011 |
| WO | WO99/45802 | 9/1999 |

OTHER PUBLICATIONS

Ahonen J.: "Vahva lihas on myös joustava lihas" May 10, 2011, downloaded Dec. 8, 2014 from http://www.terveurheilija.fi/koulutukset/iltaseminaarienmateriaalit/getfile.php??file=137, pages.

Vilja Voutilainen, Finnish Patent and Registration Office, Search Report issued in the Finnish priority application No. 20145422, pp. 1-2 plus three sheets from Google Translate.

Yu Bai et al., Review of Evidence Suggesting That the Fascia Network Could Be the Anatomical Basis for Acupoints and Meridians in the Human Body, Hindawi Publishing Corporation, Evidence-Based Complementary and Alternative Medicine, vol. 2011, Article ID 260510, 6 pages, 2011.

Anu Keski-Honkola, Finnish Patent Office as ISA, International Search Report, International Patent Application PCT/FI2015/050311, dated August 28, 2015.

Anu Keski-Honkola, Finnish Patent Office as IPEA, International Report on Patentability, International Patent Application PCT/FI2015/050311, dated Aug. 22, 2016.

* cited by examiner

GARMENT

The present application is a national stage entry, under 35 USC 371, of PCT International Patent Application Number PCT/FI2015/050311 filed on 7 May 2015, which claims priority to Finnish Patent Application Number 20145422 filed on 8 May 2014. The complete disclosures of the aforesaid International Patent Application Number PCT/FI2015/050311 and Finnish Patent Application Number 20145422 are expressly incorporated herein by reference in their entireties for all purposes.

BACKGROUND OF THE INVENTION

The invention relates to workout garments. For instance competing athletes, those interested in health exercise, and people attending to physiotherapy all need a suitable garment which enables moving, supports the body and is visually as desired.

Known garments for exercise are conventional in structure, comprising a garment sewn from a desired fabric or another material. A known kind of garment is a compression suit wherein the fabric has compression for providing a wearer with extra support.

However, the known garments as such are incapable of taking the human physiological structures into account in a sufficient manner. A known solution is disclosed in CA2756969, but the placement of the bands therein is not optimal.

BRIEF DESCRIPTION OF THE INVENTION

An object of the invention is thus to provide a garment so as to enable the aforementioned problems to be solved. The object of the invention is achieved by a garment which is characterized by what is disclosed in the independent claim. Preferred embodiments of the invention are disclosed in the dependent claims.

The idea underlying the invention is that the garment is equipped so as to enable the location of the human fascial network to be taken into account in a sufficiently good manner.

An advantage of the garment according to the invention is that it strengthens the body in a natural and safe way, thus protecting the body against musculoskeletal problems and also against postural anomalies. Tensegrity of the support network (including the fascial network) in the body is allowed to increase when it is subjected to load as the elastic reinforcements, routed in accordance with the fascial lines, that are provided in the garment resist the movement. Increasing the tensegrity results in an increase of mobility and support, i.e. stability, and in a decrease of load on the joints, and moving feels easy. The manufacturability of the garment according to the invention is good.

BRIEF DESCRIPTION OF THE FIGURES

The invention is now described in closer detail in connection with the preferred embodiments and with reference to the accompanying drawings, in which.

DETAILED DESCRIPTION OF THE INVENTION

A simple sports garment strengthening the support network of the body is provided, wherein elastic reinforcements B1, B2, B3 are sewn or otherwise attached to the textile to run in accordance with fascial lines Fl1, FL2, FL3. The number of reinforcements may be one or more, depending on the number of fascial lines to be influenced.

Next, the human HB physiology will be discussed. The fascial system in a human body mainly consists of fasciae. The fasciae are like rubber bands whose role is to keep the skeleton and the musculature together. The fascial network consisting of fascial lines transmits pressure and tension through connective tissue connections from one part of the body to another part of the body, thus maintaining the tensegrity of the body. The fascial network thus forms a tensional network which, when being loaded, grows stronger and stiffer.

The human body has several fascial lines, out of which FL1 to FL3 are shown. First, there are deep and superficial lines running on the front and the rear of the body. In addition, a spiral line winds from the direction of the lower limbs on to the body. Further, there are lateral lines, running on the sides of the body. There are also functional lines in the body on the front and the rear, the functional lines being important in powerful exertions and sports performances. The upper limbs have both superficial and deep front and rear fascial lines.

The fasciae and the muscles together form an inner "corset" of the body, which plays an important role in the well-being of the musculoskeletal system. A lack of sufficient support for the spine increases the risk of developing back troubles. A reason for poor posture is disturbances in the movement of the deep muscles and muscular weakness. The worsening of posture also causes symptoms in the neck and limb joints. As to the spinal support, timely activation of muscles would be important.

Figure 1:
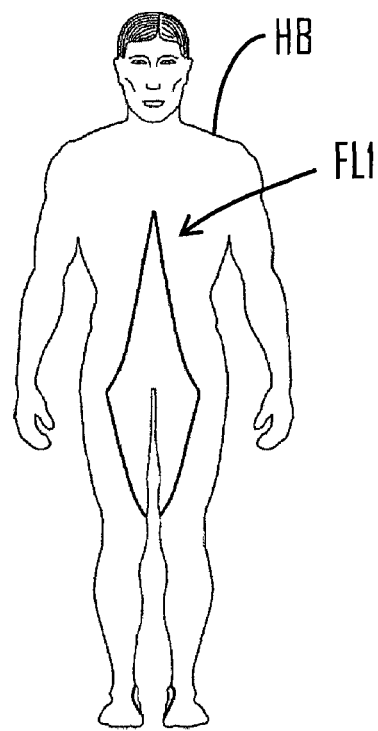
FIG. 1 shows a fascial line of a body.
Figure 2:
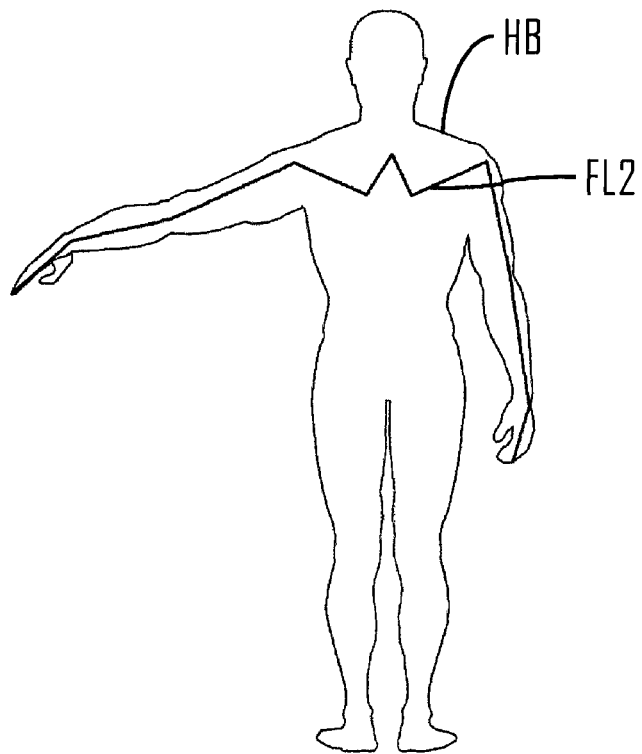
FIG. 2 shows a second fascial line of the body.
Figure 3:
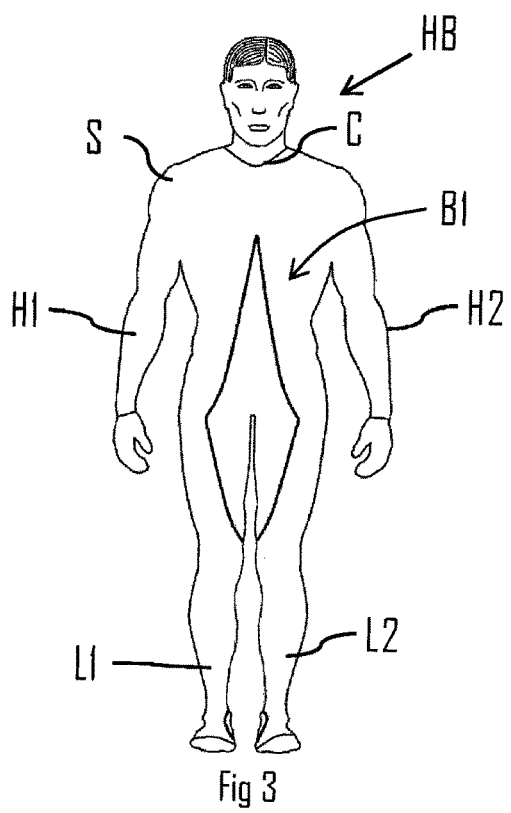
FIG. 3 shows a garment worn on the body.
Figure 4:
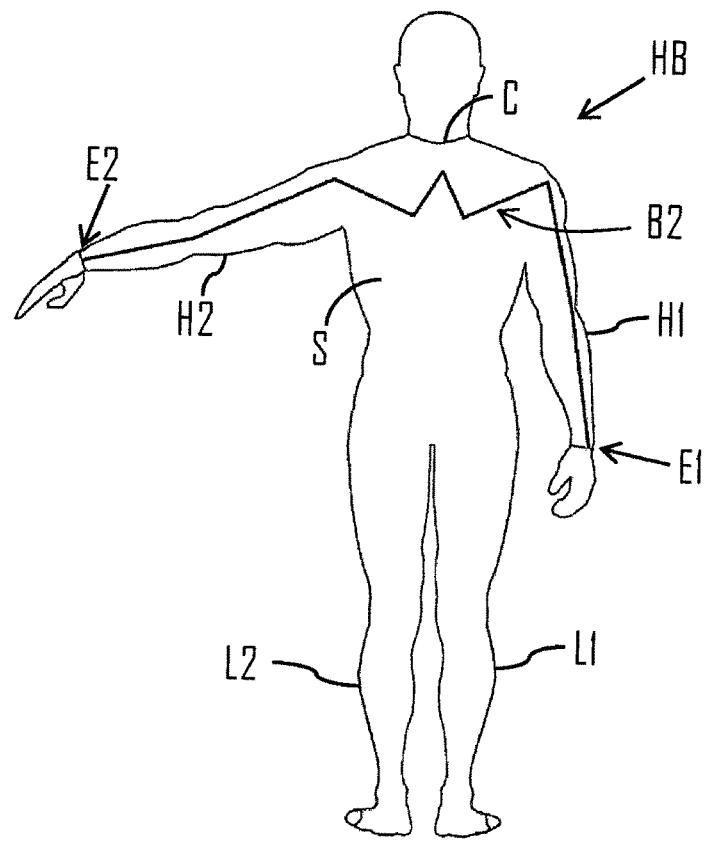
FIG. 4 shows a garment worn on the body.
Figure 8:
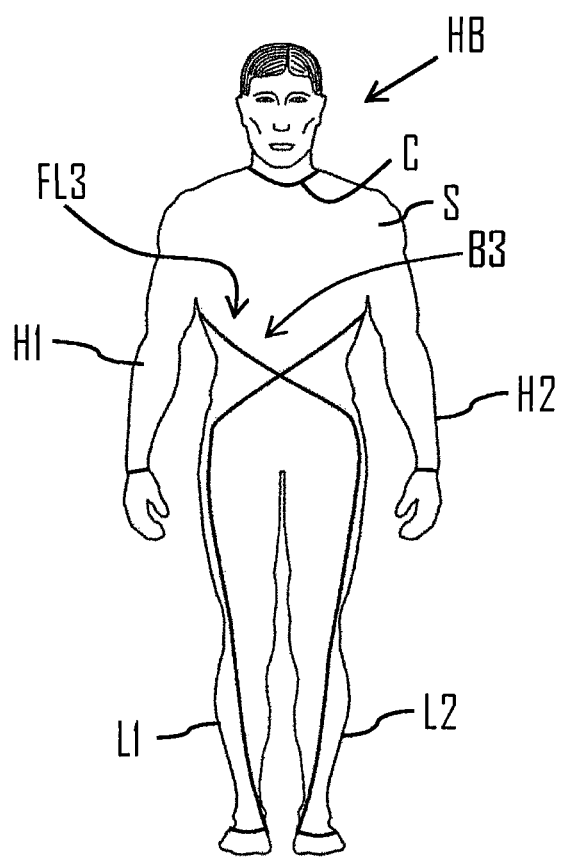
FIG. 8 shows a garment worn on the body.

FIGS. 1, 3 and 8 are front views while FIGS. 2 and 4 are rear, i.e. back, views. The invention thus relates to a garment S for sports, health exercise, physiotherapy or another performance. The garment S comprises a body part BP of the garment, and one or more limb parts H1, H2, L1, L2 of the garment which extend from the body part of the garment; in the example, sleeves are designated by H1 and H2 while legs are designated by L1 and L2, wherein the sleeves and the legs may be short or long. The body part BP may be a mere upper part, a mere lower part, or a body part of a full body suit comprising both. An edge of a collar of the garment S is designated by C in FIGS. 3, 4 and 8.

Referring particularly to FIGS. 1 to 4 and 8, the garment S comprises one or more elastic reinforcements B1, B2, B3 routed in the garment in accordance with one or more fascial lines FL1, FL2, FL3 of the human body. The fascial lines of the body are shown in FIGS. 1 to 2, while the elastic reinforcements routed in accordance therewith are shown particularly in FIGS. 3 to 4 and 8. The elastic reinforcements form a network, being provided both on a front side of the garment and a rear side of the garment. The network of the elastic reinforcements (B1 to B3) routed in accordance with the fascial lines FL1 to FL3 resides on the front side and rear side of the garment such that it winds from the front side of the garment to the rear side of the garment and/or from the rear side of the garment to the front side of the garment. In addition to or instead of the front side/rear side of the garment, an elastic band may also run on the sides of the garment.

In an embodiment, the network of the elastic reinforcements B1 to B3 routed in accordance with the fascial lines FL1 to FL3 is provided in a garment which is a full body suit comprising elastic reinforcements B1 to B3 routed in accordance with the fascial lines both in a lower part of the garment and in an upper part of the garment.

In an embodiment, this elastic reinforcement, such as B1 to B3, in accordance with the fascial line, such as FL1 to FL3, is an elastic band. The transverse width of the elastic reinforcement B1 to B3, such as a band, in accordance with the fascial line is 1 to 10 cm, for instance 5 cm. The thickness of the band may be a couple of millimetres, for instance 2 mm. The length of a single elastic reinforcement, such as B1, may be for instance 100 to 200 cm. The elastic reinforcement is a rubber-band-like flexible reinforcement arranged to load the fascial lines FL1 to FL3. In FIG. 8, the fascial line FL3 resides in the body at the elastic reinforcement B3 of the garment.

Figure 5:
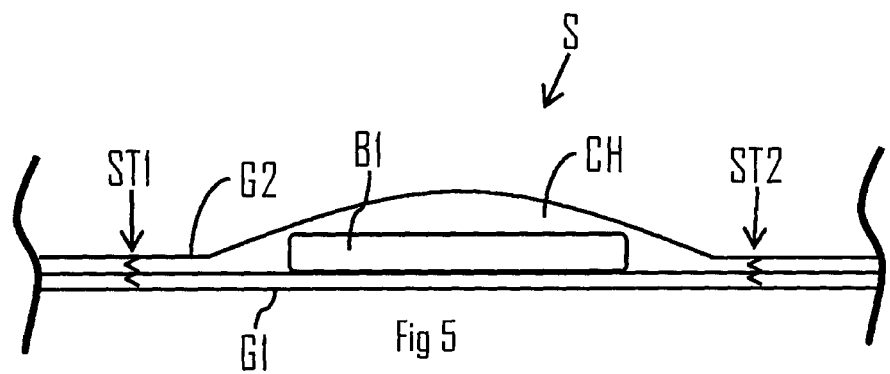
FIG. 5 shows an elastic reinforcement in a channel sewn into a garment.

It can be seen in FIG. 5 that in a preferred embodiment the elastic reinforcement B1 in accordance with the fascial line is placed in a channel CH contained in the garment. FIG. 5 shows a fabric G1 of the garment and a top fabric G2 sewn with stitches ST1, ST2 thereon for defining the channel CH in the garment S receiving the elastic reinforcement B1.

The elastic reinforcement, such as B1 to B3, is sewn to the garment, at its ends in particular, the elastic reinforcement thus being capable of resisting the movement generated by a wearer of the garment. The elastic reinforcement is attached to the garment at both ends E1, E2 of the elastic reinforcement, which are shown in FIG. 4 as for the elastic band B2.

In an embodiment, referring to FIGS. 3 to 4 and 8, the elastic reinforcement B1 in accordance with the fascial line extends from a limb part of the garment, for instance L1, to the body part BP of the garment. For example in FIG. 3, the elastic reinforcement B1 extends from the limb part L1, i.e. a leg, to the body part BP while another branch of the same elastic reinforcement B1 extends from a leg part L2, i.e. from another leg, to the body part BP. Referring to FIGS. 1 and 3, the elastic reinforcement B1 is routed in accordance with a deep frontal line FL1.

Correspondingly, in FIG. 4, the elastic reinforcement B2 extends from a limb part H2 of the garment, i.e. a sleeve H2, to the body part BP, and further to a limb part H1, i.e. in an embodiment, referring to FIGS. 2 and 4, the elastic reinforcement B2 in accordance with the fascial line is routed in accordance with a deep rear upper limb line FL2. In FIG. 4, the elastic reinforcement B2 in accordance with the fascial line is routed in accordance with the deep rear upper limb line FL2 (in FIG. 2) from the first upper limb part H1 of the garment via the upper part of the body part BP of the garment to the second upper limb part H2 of the garment.

Referring to FIG. 8, the elastic reinforcement B3 in accordance with the fascial line is routed in accordance with a spiral line FL3 from the lower limb part L1 comprised in the garment, winding on to the body part BP of the garment S and, correspondingly, from the lower limb part L2 comprised in the garment, winding on to the body part BP of the garment S.

The core of the body forms an important support for the spine. Muscles stabilize, i.e. support, the spine and posture in order to enable the posture and various movements to be carried out.

Stabilization refers to the timely tensioning of different muscle groups as well as to muscular endurance. Muscles function in chains, and they have specific counter-agents which also function in cooperating chains. Weakness and/or tightness of a muscle may change their cooperation and affect the posture. The elastic reinforcements B1 to B3 of the garment S bring joint surfaces closer, thus producing activation of muscles supporting the joint.

As regards FIGS. 1 and 3 in particular, the following can be stated. By resisting in running or walking the flexion of the shoulder joint, i.e. the bringing of the arm to the front, it is now possible by means of the disclosed garment S to activate the deep muscles in the core of the body. The garment changes the character of the movement instantly. External resistance and a proprioceptive stimulus, i.e. a stimulus caused by a sensory receptor, activate the muscles to work efficiently parallel to the resistance. The resistance produced by the elastic reinforcement, such as B1 to B3, routed in accordance with the fascial line controls the movement and produces activation of several motor units. The fasciae combine functionally the movement of the limbs, such as the upper limbs H1, H2, with the deep muscles of the body.

As regards FIGS. 2 and 4 and 8 in particular, the following can be stated. By resisting the bringing of the arms to the front, it is possible to activate the chest muscles, shoulder joint flexors and elbow joint extensors as well as increase the activation of the muscles on the flexor side of the body. By resisting the backwards movement of an upper limb, the shoulder joint flexor and the supportive muscles on the back side of the body are made stronger.

Figure 6:
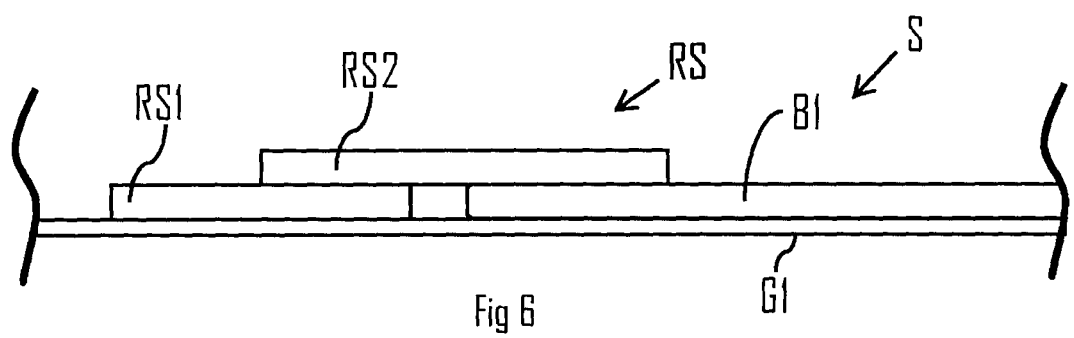
FIG. 6 shows an adjustable attachment of an end of the elastic reinforcement in the garment.

Referring to FIG. 6, the garment S comprises an adjustment structure RS for adjusting the tension of the elastic reinforcement, such as for instance B1, thus making it possible to adjust the magnitude of the resistance the elastic reinforcement B1 integrated into the garment S causes when the wearer performs movements. The adjustment structure RS comprises a part RS1 attached to the base fabric G1 of the garment and a counter-part RS2 attached to the elastic reinforcement B1. In an embodiment, the adjustment structure RS is located at an end of the elastic reinforcement. The adjustment structure RS may be provided at both ends of the elastic reinforcement, such as B1. In the example of FIG. 6, the adjustment structure RS is a so-called adhesive tape, i.e. a VELCRO® brand fastener attachment, wherein the part RS1 may be provided with small hooks closely spaced apart while the counter-part RS2 may be a part with a soft surface to which the hooks attach, providing a strong attachment. Alternatively, the adjustment structure RS may be a button joint, for instance.

As to the resisted movements, it may be further stated that the resistance generated by the elastic reinforcements B1 to B3 of the garment S increases activation on the human cortex, thus improving relearning of the movements. The resistance increases awareness of the direction of the movement and improves the control of the movement. Consequently, the garment also enables benefits to be achieved in rehabilitation for those who suffer from neurological problems.

The fascial lines, i.e. fasciae, will be discussed next to provide some background for the invention. The fasciae form routes wherein arteries, veins and lymphatic ducts run along so-called secretory and excretory channels. If the fascial network is tight, it affects metabolic processes. Today, the fasciae are tightened on account of sedentary work, for instance. The tightness of the fascial network results in functional disorders, muscular coordination disorders. The muscles are not activated in an optimal manner at an appropriate time. A poor posture and tightened fascial chains may even make breathing more difficult. The poor posture results in one fascia to stretch while the other side is tightened. The fascial network is plastic, pliable. The fascial network and chains influence the entire body. The poor posture and overload lead to poor posture and functional disorders as well. Instead of strengthening or stretching a particular muscle or muscle group, it is important to pay attention to the myofascial entity since it affects significantly an appropriate and economical way of moving and using the body as well as comprehensively the well-being of the entire body, the metabolic processes. Concomitant with the poor postures and as the metabolic disorders continue, the system continuously receives negative feedback from the body to the central nervous system, and this causes activation of the sympathetic nervous system. This may cause many kinds of irritation symptoms, restlessness, stress and functional disorders also elsewhere in the body and in the mind as well.

Figure 7:
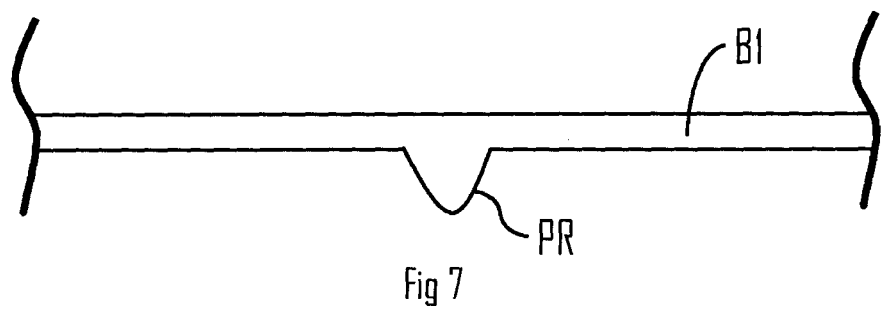
FIG. 7 shows an elastic reinforcement with a trigger point protrusion.

Referring to FIG. 7, the elastic reinforcement, such as B1 to B3, in the garment may comprise a protrusion PR on the underside, i.e. facing the body; it may be for generating pressure on a trigger point of the body. In this embodiment, the elastic reinforcement, such as B1 to B3, would thus also have another role in addition to that of the generator of motional resistance routed in accordance with the fascial lines, such as FL1. The network of the elastic reinforcements B1 to B3 routed in accordance with the fascial lines FL1 to FL3 thus comprises a protruding protrusion PR for generating pressure on a trigger point of the body.

As to the trigger point, the following is disclosed. A myofascia of the body is a covering and bonding sheet surrounding the muscles and affecting the function thereof, constituting an essential part of the fascial network. The fasciae surround all our tissues. The myofascia has trigger points that may be active or latent. With the exclusion of some exceptions, the trigger points reside at about half way through the muscle belly. An active trigger point is sensitive, painful and may refer pain to its surroundings. Sites of such referred pain may be located quite far away from the trigger point. Often the sites of referred pain follow the meridians. A latent trigger point is not actively painful but when pressure/compression is applied thereto, pain can be felt locally and be referred to its surroundings. Such latent pain points may be the reason for restriction of motion and functional disorders in muscles.

Figure 9:
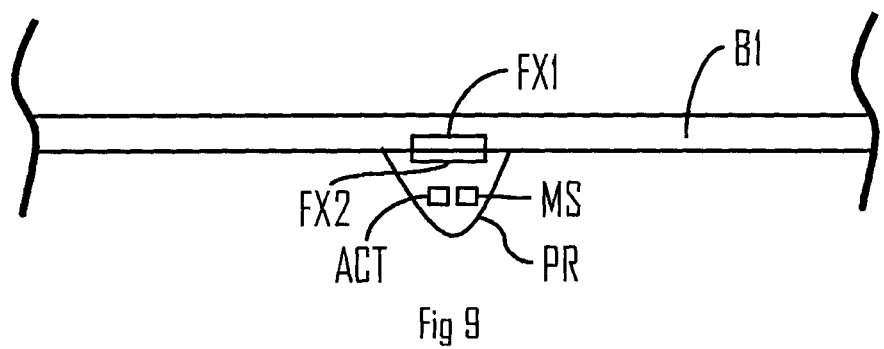
FIG. 9 shows an elastic reinforcement and a trigger point protrusion detachably attached thereto, with an actuator and a measuring sensor.

FIG. 9 shows an elastic reinforcement and a trigger point protrusion PR detachably attached thereto, with an actuator ACT and a measuring sensor MS. Said protruding protrusion PR for generating pressure on a trigger point of the body is detachably attached by an attachment arrangement FX1, FX2, making the protruding protrusion PR replaceable. This enables protrusions having protrusion of different length or a different tip shape to be readily used.

It can also be seen in FIG. 9 that an actuator ACT is provided in connection with the network of the elastic reinforcements B1 to B3 for exerting an electric, magnetic or another influence on the body of the wearer of the garment. The actuator ACR may be for instance a magnet or an electrode structure supplying an electric current to the body for the purpose of treatment, for instance, and being connected to a power supply which may be in an external device or with the garment.

According to FIG. 9, in an embodiment, this actuator provided in connection with the network of the elastic reinforcements B1 to B3 is located in the protrusion PR provided for generating pressure on the trigger point. This enables a versatile and integrated structure to be achieved.

In an embodiment, the garment is such that a measuring sensor MS is provided in connection with the network of the elastic reinforcements B1 to B3 for carrying out measurements on the body. The measuring sensor MS may be an EMG (electromyography) sensor or another sensor measuring the body, such as an optical sensor, for instance. The measuring sensor MS may be connected to a data processing unit which may be in an external device or with the garment.

In an embodiment, this measuring sensor MS provided in connection with the network of the elastic reinforcements B1 to B3 is located in the protrusion PR provided for generating pressure on the trigger point. Also in this embodiment, a versatile and integrated structure is achieved.

An integration is also possible wherein the attachment arrangement FX1, FX2 of the protruding protrusion PR is a magnetic attachment arrangement, thus forming at the same time an actuator for exerting a magnetic influence on the body, for the purpose of treatment, for instance. In such a case, a structural part FX2 performing the attachment task would thus at the same time serve as the actuator, instead of a separate actuator ACT.

It is apparent to a person skilled in the art that as technology advances, the basic idea of the invention may be implemented in many different ways. The invention and its embodiments are thus not restricted to the above-described examples but may vary within the scope of the claims.

The invention claimed is:

1. A garment comprising:
   a body part of the garment, the body part in turn including an abdominal part and left and right armpit parts; and
   left and right leg parts of the garment which extend from the body part of the garment,
   wherein the garment comprises elastic reinforcements comprising bands configured to be routed in the garment in accordance with one or more fascial lines of a human body, the elastic reinforcements forming a network and being provided both on a front side and a rear side of the garment; and
   wherein the garment is a full body suit comprising the elastic reinforcements configured to be routed in accordance with the one or more fascial lines both in a lower part of the garment and in an upper part of the garment;
   wherein the elastic reinforcements configured to be routed in accordance with the one or more fascial lines are routed in accordance with a spiral lines from the left and right leg parts comprised in the garment, winding on to the body part of the garment; and
   wherein:
      the elastic reinforcements configured to be routed in the garment in accordance with the one or more fascial lines of the human body, are configured such that, when worn by a user, the elastic reinforcements configured to be routed in the garment in accordance with the one or more fascial lines of the human body follow the one or more fascial lines for the total length of the one or more fascial lines, and
      one spiral line from the lower limb part winding onto the body part runs up an entire length of a front side of the left leg part from an inner left leg part to an outer left leg part and up and across the abdominal part from a left hip part of the left leg part up to the right armpit part, and another spiral line runs up an entire length of a front side of the right leg part from an inner right leg part to an outer right leg part and up and across the abdominal part from a right hip part of the right leg part up to the left armpit part of the garment.

* * * * *